(12) United States Patent
Mizu et al.

(10) Patent No.: US 7,790,189 B2
(45) Date of Patent: Sep. 7, 2010

(54) IMMUNOSTIMULATING AGENTS

(75) Inventors: Masami Mizu, Sakai (JP); Seiji Shinkai, Fukuoka (JP); Kazuo Sakurai, Himeji (JP); Kazuya Koumoto, Kitakyushu (JP); Munenori Numata, Fukuoka (JP); Takahiro Matsumoto, Fukuoka (JP)

(73) Assignees: Mitsui Sugar Co., Ltd., Tokyo (JP); Japan Science and Technology Agency, Saitama (JP)

( * ) Notice: Subject to any disclaimer, the term of this patent is extended or adjusted under 35 U.S.C. 154(b) by 875 days.

(21) Appl. No.: 10/557,108

(22) PCT Filed: May 13, 2004

(86) PCT No.: PCT/JP2004/006793

§ 371 (c)(1), (2), (4) Date: Jan. 16, 2007

(87) PCT Pub. No.: WO2004/100965

PCT Pub. Date: Nov. 25, 2004

(65) Prior Publication Data

US 2008/0262210 A1   Oct. 23, 2008

(30) Foreign Application Priority Data

May 15, 2003   (JP)   ............................. 2003-136876

(51) Int. Cl.
- A61K 45/00   (2006.01)
- A61K 38/16   (2006.01)
- A61K 31/70   (2006.01)
- A61K 31/715   (2006.01)
- A01N 43/04   (2006.01)

(52) U.S. Cl. ................ 424/278.1; 424/279.1; 514/44 A; 514/8; 514/23; 514/54

(58) Field of Classification Search ........................ None
See application file for complete search history.

(56) References Cited

U.S. PATENT DOCUMENTS

| | | | |
|---|---|---|---|
| 5,962,636 A * | 10/1999 | Bachmaier et al. | ........... 530/326 |
| 6,194,388 B1 * | 2/2001 | Krieg et al. | ................ 514/44 A |
| 6,207,646 B1 | 3/2001 | Krieg | |
| 6,214,806 B1 | 4/2001 | Krieg | |
| 6,218,371 B1 * | 4/2001 | Krieg et al. | ................ 514/44 R |
| 6,225,292 B1 | 5/2001 | Raz | |
| 6,239,116 B1 * | 5/2001 | Krieg et al. | ................ 514/44 A |
| 6,406,705 B1 * | 6/2002 | Davis et al. | ............... 424/278.1 |
| 6,465,438 B1 | 10/2002 | Schorr | |
| 6,558,670 B1 * | 5/2003 | Friede et al. | ............. 424/184.1 |
| 6,589,940 B1 | 7/2003 | Raz | |
| 6,949,520 B1 | 9/2005 | Hartmann | |
| 6,994,959 B1 | 2/2006 | Tam | |
| 7,118,480 B2 | 10/2006 | Aoki | |
| 7,208,478 B2 | 4/2007 | Carson | |
| 7,537,767 B2 * | 5/2009 | Bachmann et al. | ....... 424/185.1 |
| 2001/0034330 A1 * | 10/2001 | Kensil | ......................... 514/44 |
| 2002/0064515 A1 * | 5/2002 | Krieg et al. | ................ 424/85.1 |
| 2002/0086839 A1 | 7/2002 | Raz | |
| 2004/0008338 A1 * | 1/2004 | Detweiler et al. | ......... 356/141.1 |
| 2004/0052763 A1 * | 3/2004 | Mond et al. | ................ 424/93.2 |
| 2006/0084149 A1 | 4/2006 | Kimura | |
| 2007/0066554 A1 | 3/2007 | Krieg | |
| 2008/0262210 A1 * | 10/2008 | Mizu et al. | ................. 536/23.1 |
| 2009/0202575 A1 * | 8/2009 | Krieg et al. | .............. 424/184.1 |
| 2009/0263413 A1 * | 10/2009 | Iwamura et al. | .......... 424/189.1 |

FOREIGN PATENT DOCUMENTS

| | | | |
|---|---|---|---|
| CA | 2145664 | | 8/2002 |
| CA | 2189831 | | 1/2006 |
| CA | 2194761 | | 12/2006 |
| EP | 468520 A | * | 1/1992 |
| EP | 855184 A1 | * | 7/1998 |
| EP | 1625850 A1 | * | 2/2006 |
| JP | 1992352724 A | * | 12/1992 |
| JP | 2006069913 | * | 3/2006 |
| JP | 2007070307 | * | 3/2007 |
| JP | 2007070307 A | * | 3/2007 |
| JP | 2007314452 | * | 12/2007 |
| JP | 2008100919 | * | 5/2008 |
| WO | WO 96/14873 A3 | * | 5/1996 |
| WO | WO 97/40163 A1 | * | 10/1997 |
| WO | WO 98/18810 A1 | * | 5/1998 |

(Continued)

OTHER PUBLICATIONS

Sakurai et al, In: Non-viral Gene Therapy, 2005, ed: Tiara et al, pp. 103-117.*

(Continued)

*Primary Examiner*—N. M Minnifield
(74) *Attorney, Agent, or Firm*—Fay Sharpe LLP

(57) ABSTRACT

Disclosed is a new type of immunostimulating agent including an immunostimulating oligonucleotide complexed with a carrier which is safe and has a high transfection effect. The carrier complexed with the immunostimulating oligonucleotide to form the immunostimulating agent is a polysaccharide having β-1,3-bonds (preferably β-1,3-glucan such as schizophyllan). A preferred example of the immunostimulating oligonucleotide is one containing an unmethylated CpG motif. The polysaccharide for use is preferably modified with nucleic acid-binding functional group and/or cell membrane-affinitive functional group.

9 Claims, 11 Drawing Sheets

FOREIGN PATENT DOCUMENTS

| | | | |
|---|---|---|---|
| WO | WO 99/33488 A2 | * | 7/1999 |
| WO | WO 99/51259 A2 | * | 10/1999 |
| WO | WO 99/56755 A1 | * | 11/1999 |
| WO | WO 99/58118 A2 | * | 11/1999 |
| WO | WO 00/20039 | | 4/2000 |
| WO | WO 01/22990 A | * | 4/2001 |
| WO | WO 01/34207 | | 5/2001 |
| WO | WO 01/93902 A | * | 12/2001 |
| WO | WO 03/024481 A | * | 3/2003 |
| WO | WO 2004/100965 A1 | * | 11/2004 |
| WO | WO 2004/100965 A1 | * | 11/2004 |
| WO | WO 2007/095316 | * | 8/2007 |
| WO | WO 2009/068996 | * | 6/2009 |

OTHER PUBLICATIONS

Takeda et al, Biomacromolecules, 2007, 8:1178-1186.*
Anada et al, Bioorganic & Medicinal Chemistry Letters, 2006, 16:1301-1304.*
Sakurai et al, Chem. Commun., 2005, pp. 4383-4398.*
Mizu et al, Chem. Commun., 2001, pp. 429-430.*
Shimada et al, Biocongjuate Chem., 2007, 18:1280-1286.*
Shimada et al, Bioconjugate Chem., 2006, 17:1136-1140.*
Mizu et al, J. Am. Chem. Soc., 2004, 126:8372-8373.*
Koumoto et al, Chem. Commun., 2001, pp. 1962-1963.*
Matsumoto et al, BBA, 2004, 1670:91-104.*
Minari et al, Chemistry Letters, 2008, 37/1:92-93.*
Ikeda et al, Org. Biomol. Chem., 2007, 5:2219-2224.*
Sakuari et al, Polymer Preprints, 2004, 45/2:457-458.*
Takahisa et al, Trends in Glycoscience and Glycotechnology, Mar. 2005, 17/94:49-57.*
Sakurai et al, $228^{th}$ ACS National Meeting, 2004, abstract only.*
Aramaki et al, Biol Pharm. Bull., 2002, 25/3:351-355.*
Takeda et al, $232^{nd}$ ACS National Meeting, 2006, abstract only.*
Minari et al, Oligonucleotides, 2008, 18/4:337-344.*
Krieg, Trends in Microbiology, Jun. 2001, 9/6:249-252.*
Verthelyi et al, Clinical Immunology, 2003, 109:64-71.*
Lin et al, J. Invest. Medicine, Sep. 1997, 45/7:333A abstract only.*
Yamamoto et al, Antisense Research and Development, 1994, 4:119-122.*
Krieg et al, Immunology Today, 2000, 21/10:521-526.*
McCluskie et al, Mol. Med., 1999, 5/5:287-300.*
U.S. 6,008,200, (withdrawn).*
Matsumato et al, BBA, 2004, 1670:91-104.*
Boussif, et al., Gene Therapy, 3, 1074-1080 (1996).
Crystal, Science, 270, 404-410 (1995).
Gürsel, et al., Journal of Leukocyte Biology, 72, 813-820, May 2002.
Ishii, et al., Langmuir, 17, 5825-5833 (2001).
Kimura, et al., Chem. Lett., 1242 (2000).
Klinman, et al., Proc. Natl. Acad. Sci., 93, 2879-2883, Apr. 1996.
Krieg, et al., Nature, 374, 576 (1995).
Martin, et al., Am. Chem. Soc. Polymer Prep., 38(1), 253-254 (1997).
McIntire, et al., J. Am. Chem. Soc., 120, 669 (1998).
Miller, Nature, 357, 455-460 (1992).
Mulligan, Science, 260, 926-932 (1993).
Numata, et al., Bioorg. Chem., 31, 163-171 (2003).
Sakurai, et al., J. Am. Chem. Soc., 122, 4520 (2000).
Tabata, et al., Carbohydr., 89, 121-135 (1981).
Tokunaga, et al., J. Natl. Cancer Inst., 72, 955 (1984).
Tokunaga, et al., J. Natl. Cancer Res., 79, 682 (1988).
Tomlinson, et al., J. Contr. Rel., 39, 357-372 (1996).

* cited by examiner

FIG.2

R8
NH$_2$-Cys-Arg-Arg-Arg-Arg-Arg-Arg-Arg-Arg-COOH  (SEQ ID NO 2)

RGD
NH$_2$-Cys-Arg-Gly-Asp-COOH  (SEQ ID NO 3)

SEQUENCE LISTING

```
<160> NUMBER OF SEQ ID NOS: 17

<210> SEQ ID NO 1
<211> LENGTH: 60
<212> TYPE: DNA
<213> ORGANISM: Artificial Sequence
<220> FEATURE:
<223> OTHER INFORMATION: Solid phase synthesized nucleotide

<400> SEQUENCE: 1
tccatgacgt tcctgatgct aaaaaaaaaa aaaaaaaaaa aaaaaaaaaa aaaaaaaaaa        60

<210> SEQ ID NO 2
<211> LENGTH: 3
<212> TYPE: PRT
<213> ORGANISM: Artificial Sequence
<220> FEATURE:
<223> OTHER INFORMATION: Solid phase synthesized peptide

<400> SEQUENCE: 2

Arg Gly Asp
1

<210> SEQ ID NO 3
<211> LENGTH: 8
<212> TYPE: PRT
<213> ORGANISM: Artificial Sequence
<220> FEATURE:
<223> OTHER INFORMATION: Solid phase synthesized peptide

<400> SEQUENCE: 3

Arg Arg Arg Arg Arg Arg Arg Arg
1               5

<210> SEQ ID NO 4
<211> LENGTH: 60
<212> TYPE: DNA
<213> ORGANISM: Artificial Sequence
<220> FEATURE:
<223> OTHER INFORMATION: Artificial S-oligonucleotide

<400> SEQUENCE: 4
tccatgagct tcctgatgct aaaaaaaaaa aaaaaaaaaa aaaaaaaaaa aaaaaaaaaa        60
```

```
<210> SEQ ID NO 5
<211> LENGTH: 60
<212> TYPE: DNA
<213> ORGANISM: Artificial Sequence
<220> FEATURE:
<223> OTHER INFORMATION: Solid phase synthesized nucleotide

<400> SEQUENCE: 5
tccatgacgt tcctgatgct aaaaaaaaaa aaaaaaaaaa aaaaaaaaaa aaaaaaaaaa       60

<210> SEQ ID NO 6
<211> LENGTH: 60
<212> TYPE: DNA
<213> ORGANISM: Artificial Sequence
<220> FEATURE:
<223> OTHER INFORMATION: Solid phase synthesized nucleotide

<400> SEQUENCE: 6
tccatgagct tcctgatgct aaaaaaaaaa aaaaaaaaaa aaaaaaaaaa aaaaaaaaaa       60

<210> SEQ ID NO 7
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 7
accgataccg gtgccggtga cggcaccacg                                        30

<210> SEQ ID NO 8
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 8
accgatagcg ctgccggtga cggcaccacg                                        30

<210> SEQ ID NO 9
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 9
accgatgacg tcgccggtga cggcaccacg                                        30

<210> SEQ ID NO 10
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 10
accgattcgc gagccggtga cggcaccacg                                        30

<210> SEQ ID NO 11
<211> LENGTH: 30
<212> TYPE: DNA
<213> ORGANISM: Artificial Sequence
<220> FEATURE:
```

```
<223> OTHER INFORMATION: immunostimulating oligonucleotide

<400> SEQUENCE: 11
gggggggggg ggcgatcggg gggggggggg                                    30

<210> SEQ ID NO 12
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 12
gggggggggg gacgatcgtc gggggggggg                                    30

<210> SEQ ID NO 13
<211> LENGTH: 30
<212> TYPE: DNA
<213> ORGANISM: Artificial Sequence
<220> FEATURE:
<223> OTHER INFORMATION: immunostimulating oligonucleotide

<400> SEQUENCE: 13
gggggggggg ggaacgttgg gggggggggg                                    30

<210> SEQ ID NO 14
<211> LENGTH: 20
<212> TYPE: DNA
<213> ORGANISM: Artificial Sequence
<220> FEATURE:
<223> OTHER INFORMATION: immunostimulating oligonucleotide

<400> SEQUENCE: 14
gagaacgctc gaccttcgat                                               20

<210> SEQ ID NO 15
<211> LENGTH: 20
<212> TYPE: DNA
<213> ORGANISM: Artificial Sequence
<220> FEATURE:
<223> OTHER INFORMATION: immunostimulating oligonucleotide

<400> SEQUENCE: 15
tccatgacgt tcctgatgct                                               20

<210> SEQ ID NO 16
<211> LENGTH: 18
<212> TYPE: DNA
<213> ORGANISM: Artificial Sequence
<220> FEATURE:
<223> OTHER INFORMATION: immunostimulating oligonucleotide

<400> SEQUENCE: 16
tctcccagcg tgcgccat                                                 18

<210> SEQ ID NO 17
<211> LENGTH: 20
<212> TYPE: DNA
<213> ORGANISM: Artificial Sequence
<220> FEATURE:
<223> OTHER INFORMATION: immunostimulating oligonucleotide

<400> SEQUENCE: 17
ggggtcaacg ttgagggggg                                               20
```

IMMUNOSTIMULATING AGENTS

TECHNICAL FIELD

The present invention belongs to the technical field of an immunostimulating agent (which may also be called an immunostimulant, immunoactivator or immunoaccelerator) and particularly relates to the provision of a safe and efficacious immunostimulating agent obtained by complexing an immunological oligonucleotide with a novel transfection agent.

BACKGROUND ART

An oligonucleotide which is active in stimulating immunoresponse (hereinafter sometimes referred to as an immunostimulating oligonucleotide, immunostimulating nucleic acid or immunostimulating DNA) was discovered by T. Tokunaga and others in 1984 in the course of a search for antitumoral substances against BCG. It was then elucidated that the activity is due to a specific base sequence containing a dinucleotide of cytosine and guanine (5'-CpG-3': the so-called CpG sequence) (Tokunaga, T., et al., J. Natl, Cancer Inst., 72, 955 (1984): Non-patent Reference 1; Tokunaga, T., et al., J. Natl. Cancer Res., 79, 682 (1988): Non-patent Reference 2).

Genome DNAs containing a CpG sequence present in organisms other than vertebrates and plants are also found to have a similar activity. It is considered that a sequence around the CpG core is also important in immunostimulation activity. Particularly, the sequence of 5'-PuPuCpGPyPy-3', in which unmethylated CpG is sandwiched by substituted purines (Pu) and substituted pyrimidines (Py), is recognized as a typical unmethylated CpG motif (Krieg, A., et al., Nature, 374, 576 (1995): Non-patent Reference 3). As well known, a CpG motif is defined as a short nucleotide sequence (generally, a sequence of four to ten nucleotides) containing at least one cytosine (C)-guanine (G) sequence in which the 5' position of the cytosine in the cytosine-guanine sequence is not methylated. Hereinafter, CpG is used to mean unmethylated CpG unless otherwise noted.

Examples of useful CpG motifs (hexamers) are given below, wherein A denotes adenine, G guanine, T thymine, and U uracil, respectively:

AACGTT, AGCGTT, GACGTT, GGCGTT, AACGTC, AGCGTC,

GACGTC, GGCGTC, AACGCC, AGCGCC, GACGCC, GGCGCC,

AACGCT, AGCGCT, GACGCT, GGCGCT

An oligonucleotide of 8 to 100 nucleotides containing an above-mentioned sequence has an immunostimulation activity (Japanese Patent Application Publication No. 2001-503254: Patent Reference 1)

The following are examples of immunostimulating oligonucleotides containing a CpG motif, which have been reported as being effective in activating NK cells, wherein the underlined parts show a CpG motif and the parts with capital letters denote a thiolated DNA (Iho, S., and Yamato, S., Annual Review Immunity, 2001, 137-146(2002): Non-patent Reference 4):

| | |
|---|---|
| accgat<u>accggt</u>gccggtgacggcaccacg | (SEQ ID NO 7) |
| accgat<u>agcgct</u>gccggtgacggcaccacg | (SEQ ID NO 8) |
| accgatgacgtcgccggtgacggcaccacg | (SEQ ID NO 9) |
| accgat<u>tcgcgag</u>ccggtgacggcaccacg | (SEQ ID NO 10) |
| gggggggggggg<u>cgatcg</u>gggggggggggg | (SEQ ID NO 11) |
| ggggggggggg<u>gacgatcgt</u>cggggggggg | (SEQ ID NO 12) |
| gggggggggggg<u>aacgtt</u>gggggggggggg | (SEQ ID NO 13) |
| GAG<u>AACGCT</u>CGACCTTCGAT | (SEQ ID NO 14) |
| TCCAT<u>GACGTT</u>CCTGATGCT | (SEQ ID NO 15) |
| TCTCCCAG<u>CG</u>TG<u>CG</u>CCAT | (SEQ ID NO 16) |
| GGggt<u>caacgtt</u>gaGGGGGg | (SEQ ID NO 17) |

There are known several types of sequences as immunostimulating nucleic acids other than CpG motifs. Examples include a T-rich nucleic acid such as 5'TTT3' which is rich in thymidine, a G-rich nucleic acid such as 5'GGGG3' which is rich in guanidine, a TG-rich nucleic acid which is rich in thymidine and guanidine, and a C-rich nucleic acid which is rich in cytidine. Recently these sequences have received considerable attention as non-CpG immunostimulating nucleic acids (Japanese Patent Application Publication No. 1996-500738: Patent Reference 2; Japanese Patent Application Publication No. 2002-512599: Patent Reference 3; Japanese Patent Application Publication No. 2003-51028: Patent Reference 4; Japanese Patent Application No. 2003-510290: Patent Reference 5).

A characteristic effect of the above-mentioned immunostimulating nucleic acids on immunocytes is that they activate antigen presenting cells. They act directly upon such cells as monocytes, macrophages or dentritic cells to produce immunoenhancing cytokines such as IL-6, TNF-α, IL-12, IFNα/β, IL-18 or nitrogen monoxide.

Recently there has been seen an increase in the number of patent applications on nucleic acids for therapeutic purposes or DNA vaccine compositions against immunological diseases. For example, the University of Iowa Research Foundation has proposed a number of sequences based on CpG motifs for use in therapies on adjuvants against diseases or disorders, including immunodeficiencies caused by infections with viruses, bacteria, fungi or parasites, cancers, or acute reduction in the air current due to exposure to lipopolysaccharides or endotoxins (Japanese Patent Application Publication No. 1998-506265: Patent Reference 6; Japanese Patent Application Publication No. 2001-503267: Patent Reference 7; Japanese Patent Application No. 2001-513776: Patent Reference 8).

A patent application is found on the use of a CpG motif in DNA vaccines for fishery products (Japanese Patent Application Publication No. 1997-285291: Patent Reference 9).

A patent application has also been filed on the use of a CpG motif for preventive purposes against infection with parvovirus in animals (Japanese Patent Application No. 2000-509976).

Aside from that set out in Patent Reference 1, a number of sequences exhibiting an immunostimulant activity are also set out in patent applications such as Patent References 11 and 12 (Japanese Patent Application Publication No. 2002-517156: Patent Reference 11; Japanese Patent Application No. 2002-526425: Patent Reference 12).

As in the case of gene therapy using an antisense DNA, an immunostimulating nucleotide is often modified so that the phosphodiester bonds at its phosphoric acid backbone are converted to phosphorothioate bonds so as to be imparted with resistance against nuclease. Besides, it is often a case that an oligonucleotide is used concurrently with a transfection agent such as a liposome, cationic lipid, or cholesterol, for the purpose of enhancing the affinity with cells.

Some retroviruses and adenoviruses provided, at the beginning, a promising prospect in vitro as a transfection agent for antisense DNAs in gene therapy. However, their uses are now very limited because of their inflammatory and immunogenic nature as well as the risk of mutagenesis and integration with the genome due to such naturally occurring viruses (Mulligan, Science, 260, 926-932 (1993): Patent Reference 5; Miller, Nature, 357, 455-460 (1992): Patent Reference 6; Crystal, Science, 270, 404-410 (1995): Patent Reference 7).

As an alternative to such natural types of transfection agents for genes, there is proposed an artificial and nonviral carrier, which is easy to handle as compared with viruses and enables assured and efficient introduction of DNAs into cells (Tomlinson and Rolland, J. Contr. Rel., 39, 357-372 (1996): Patent Reference 8).

The nonviral, artificial carrier now under extensive studies is polyethyleneimine (PEI). PEI is a cationic polymer, which assumes a three-dimensional branched structure in a variety of adherent cell or suspended cell lines, that can achieve a transfection efficiency above average in some cases (Boussif et al., Gene Therapy, 3, 1074-1080 (1996): Non-patent Reference 9).

There have been many patent applications on various types of cationic polymers or cationic lipids, modified with a substituent containing nitrogen atom as in PEI, filed under titles such as gene carrier, transfection agent, pharmaceutical support and the like.

However, the present situation is that almost no investigation has been made on the safety of cationic polymers including PEI. While the presence of amino group(s) is generally indispensable in order to render a substance cationic, the substance with amino group(s) is highly bioactive and has a risk of toxicity in the body. As a matter of fact no cationic polymers studied so far have been put into practical use or listed in dictionaries on pharmaceutical additives or the like (The Pharmaceutical Additives Dictionary, Edited by Pharmaceutical Additives Association of Japan, Published by Yakujinipposha: Non-patent Reference 11).

β-1,3-glucan is a polysaccharide which has been put into clinical use in intramuscular injection. It has been long known that this polysaccharide assumes a triple helix structure as it occurs naturally (Theresa M. McIntire and David A. Brant, J. Am. Chem. Soc., 120, 699 (1998): Non-patent Reference 12). The in vivo safety of this polysaccharide has already been confirmed since it has been actually put into practice over twenty years as a intramuscular injection in the immunological enhancement treatment against gynaecological cancer (Shimizu et al., Biotherapy, 4, 1390 (1990): Non-patent Reference 13; Hasegawa, Oncology and Chemotherapy, 8, 225 (1992): Non-patent Reference 14).

The prior art includes conjugation of β-1,3-glucan with a biomaterial such as DNA for use as a gene carrier. This prior art relates to the preparation of a conjugate of β-1,3-glucan and a bioactive material in which β-1,3-glucan of triple helix structure as it naturally occurs is bonded to the bioactive material through covalent linkage (PCT/US95/14800: Patent Reference 13).

Recently, the present inventors and others have discovered that a polysaccharide having β-1,3-bonds in the backbone forms a new type of complex with various nucleic acids when subjected to a specific artificial treatment (PCT/JP00/07875: Patent Reference 14; PCT/JP02/02228: Patent Reference 15; Sakurai, K., et al., J. Am. Chem. Soc., 122, 4520 (2000): Non-patent Reference 15; Sakurai, K., et al., Chem. Lett., 1242 (2000): Non-patent Reference 16).

The object of the present invention is to provide an immunostimulating agent in which an immunostimulating oligonucleotide is complexed with a new type of carrier which is safe and has a high transfection efficiency.

DISCLOSURE OF THE INVENTION

The present inventors have discovered that, by the utilization of a polysaccharide having β-1,3-bonds as a carrier (transfection agent), there can be obtained an immunostimulating agent which is safe and serves to increase the function of an immunostimulating oligonucleotide for excellent immunological enhancement.

Thus, according to the present invention there is provided an immunostimulating agent which comprises a complex of an immunostimulating oligonucleotide and a polysaccharide having β-1,3-bonds.

BRIEF DESCRIPTION OF THE DRAWINGS

FIG. 2 shows the amino acid sequences of R8 peptide (SEQ ID NO 2) and RGD peptide (SEQ ID NO 3) for use in the present invention.

BEST MODE FOR CARRYING OUT THE INVENTION

Figure 1:
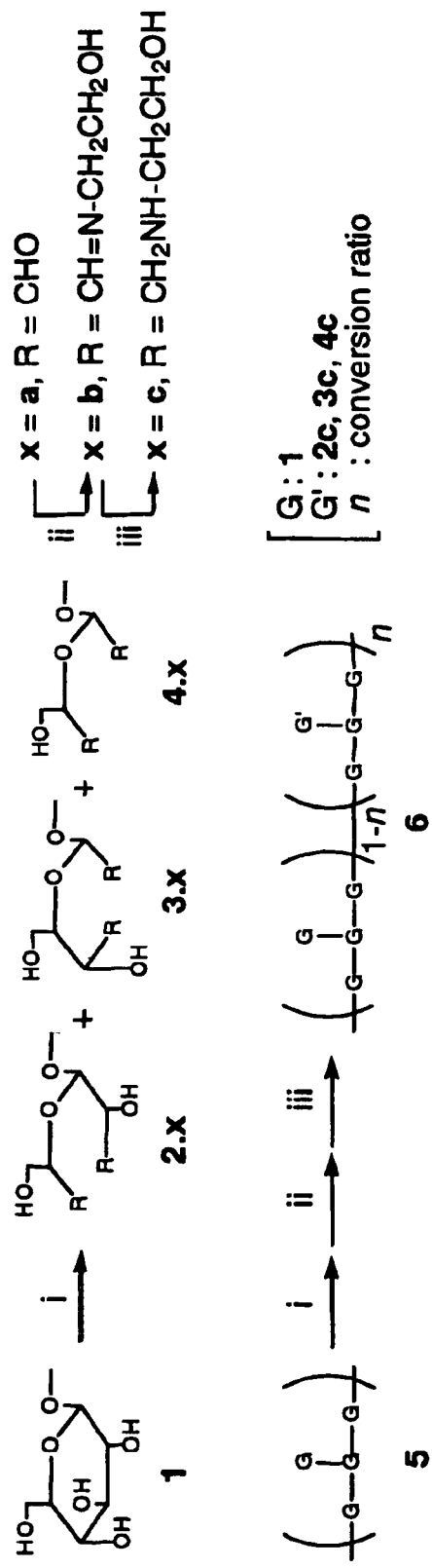
FIG. 1 shows a reaction scheme for synthesizing a modified polysaccharide for use in the present invention, as an example, in which a cationic functional group is introduced into a polysaccharide.

In the present invention an immunostimulating oligonucleotide is used as the main agent. The immunostimulating oligonucleotide for use in the present invention is an oligonucleotide which stimulates the immune response to enhance immunity, and is exemplified by a variety of oligonucleotides as described in the aforementioned references, but is not limited thereto. As the immunostimulating oligonucleotide to which the present invention is directed, is preferably used an oligonucleotide containing an unmethylated CpG motif, a variety of which are described in the aforesaid references. There can be also used a non-CpG type of immunostimulating oligonucleotide (an immunostimulating oligonucleotide other than CpG motif), examples of which are also described in the foregoing. Such non-CpG immunostimulating oligonucleotide can be utilized alone or in combination with CpG motif(s). These oligonucleotides, when administered, act on immunocytes such as macrophage to enhance immunity through the production of cytokines and other functions.

For an increased resistance to nuclease, the phosphoric acid backbone of the oligonucleotide for use in the present invention is generally modified so that the phosphodiester bonds at the backbone are converted to phosphorothioate or phosphorodithioate bonds. An oligonucleotide having all or a part of the phosphodiester bonds unconverted may also be utilized.

The immunostimulating agent of the present invention comprises a complex of an immunostimulating agent such as mentioned above and a polysaccharide having $\beta$-1,3-bonds, in which the polysaccharide serves as a transfection agent. Preferred polysaccharides having $\beta$-1,3-bonds for use in the present invention are $\beta$-1,3-glucan and $\beta$-1,3-xylan. Particularly preferred is $\beta$-1,3-glucan selected from among schizophyllan, lentinan, scleroglucan, curdlan, pachyman, grifolan and laminaran. Above all, is preferred $\beta$-1,3-glucan having plenty of 1,6-glucopyranoside branches, such as schizophyllan, lentinan or scleroglucan (branching rate: 33-40%).

While the polysaccharide for use in the present invention mentioned above may be used as it is native, it is more preferred for the polysaccharide to be modified with nucleic acid-binding and/or cell membrane-affinitive functional groups. By "nucleic acid-binding" is meant the function to interact a nucleic acid so as to enhance the binding between the polysaccharide and the nucleic acid. By "cell membrane-affinitive" is meant affinitive with cell membrane proteins and cell membrane lipids (phospholipids). In the present invention there is preferably used a polysaccharide which is modified with one or both of nucleic acid-binding functional group and cell membrane-affinitive group. Particularly preferred examples of the nucleic acid-binding and/or the cell membrane-affinitive functional groups include a cationic functional group, a steroid-based functional group, a basic amino acid-based functional group, and peptide-based functional group.

A cationic functional group is defined by a functional group having positive electric charge (cf. Working Example 2 set out later, for a concrete example). The polysaccharide, when provided with cationic functional groups, has enhanced binding to a nucleic acid through the electrostatic interaction between the positive charge and the negative charge possessed by the nucleic acid such as DNA and RNA. A steroid-based functional group (a concrete example of which is given in Working Example 4 later,) provides the nucleic acid-binding effect by positive charge due to amino acid groups bonded to the steroid ring via a spacer, as well as the cell membrane-affinitive effect due to the steroid ring. A basic amino acid-based functional group, a concrete example of which is given in Working Example 3 set out later, provides the nucleic acid-binding effect by positive charge due to amino groups of the amino acid, as well as the cell membrane-affinitive effect due to the basic amino acid residue. As exemplified by R8 or RGD described in Working Examples 5-7, a peptide-based functional group is a peptide chain containing an amino acid sequence which will promote the transfection of a nucleic acid primarily due to the affinity to cell membrane.

The polysaccharides can be modified so as to be introduced with the above-mentioned nucleic acid-binding and/or cell membrane-affinitive functional groups in an ordinary manner known in the field of organic chemistry. Generally, the polysaccharide is subjected to periodate oxidation of its 1,6-glucopyranoside branches, followed by reductive amination (cf. FIG. 1). While the details on the reactions are given in PCT/JP02/02228 (Patent Reference 15) by the present inventors, the following is the substance thereof.

In order to obtain the modified polysaccharide composing the immunostimulating agent of the present invention, the polysaccharide is provided with the nucleic acid-binding and/or cell membrane-affinitive functional groups generally by periodate oxidation of the 1,6-glucopyranoside branches followed by reductive amination, as mentioned above.

Thus, the nucleic acid-binding functional group and the cell membrane-affinitive functional group for forming the modified polysaccharide for use in the present invention are derived from compounds having a primary amine, secondary amine or hydrazine moiety, to which reductive amination can be applied.

For example, preferred examples of the cationic functional group for use in the present invention include, but are not limited to, those as shown in the following, which are derived from chain or cyclic compounds containing at least one primary or secondary amino group. They can be easily synthesized from commercially available compounds containing an amino group or groups.

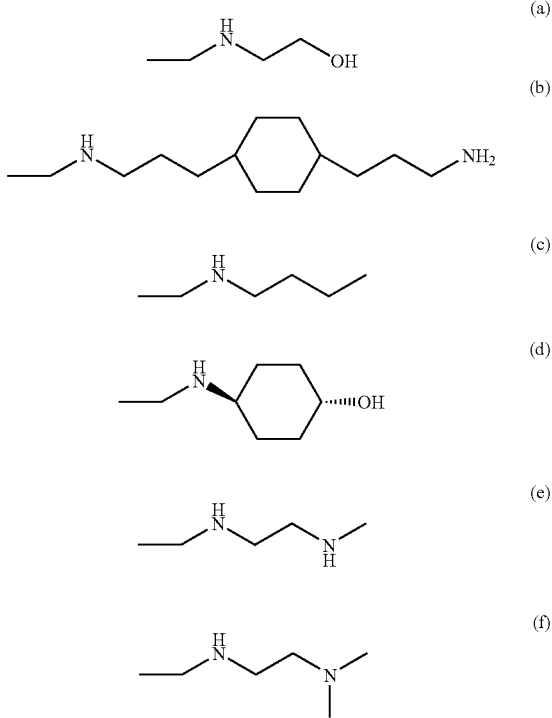

FIG. 1 illustrates a process for preparing the cationically modified polysaccharide for use in the present invention, in which a cationic functional group (the above-mentioned (a)) is introduced as the nucleic acid-binding functional group, as an example. In the figure, (i) denotes the step of the oxidation with a periodate, (ii)

the Schiff base with sodium borohydride. In the case of (β-1,3-glucan having branches containing an unreacted hydroxyl group at the 3-position, there are obtained products as expressed by 2.X, 3.X, and 4.X. The reactions occur at the branch or side chain as shown by 5 and 6 in the figure.

The steroid-based functional groups to be introduced into the polysaccharide for use in the present invention by the reductive amination following the periodate oxidation are preferably those derived from the compounds expressed by the formula (2): a compound having a steroid ring to which an amino group or groups are bonded via a spacer.

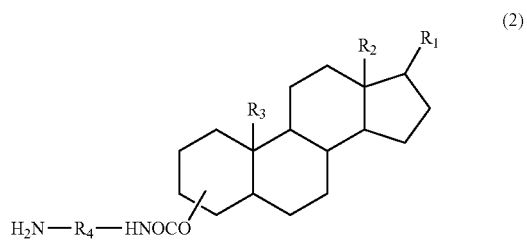

In the formula, $R_1$, $R_2$ and $R_3$ independently express hydrogen atom or a substituent containing carbon, oxygen, nitrogen and/or hydrogen atom(s). $R_4$ denotes a spacer moiety which is hydrogen atom or is derived from a chain or cyclic compound containing carbon, oxygen, nitrogen and/or hydrogen atom(s). The atomic group containing $R_4$ may be bound to any position of the steroid ring. A compound falling outside the above-mentioned general formula may also be used, provided that it contains a steroid ring, as exemplified by a corticosterone or cortisol derivative.

Such steroid-based functional group may be introduced into the polysaccharide in the following manner: The hydroxyl bond to the steroid ring is caused to react with a diamine, followed by the introduction of the steroid-based functional group into the branches of β-1,3-glucan by the reductive amination as mentioned earlier.

The basic amino acid-based functional groups to be introduced into the branches of the polysaccharides for use in the present invention by the periodate oxidation and the reductive amination are those derived from an amino acid as expressed by the following general formula (3):

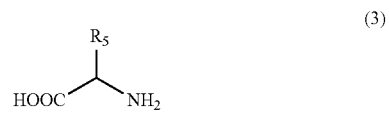

In the formula, $R_5$ denotes the side chain of amino acid. The basic amino acid is introduced into the branches of the polysaccharide, with the carboxyl group and the side chain thereof being protected.

The preparation of the complex of the immunostimulating oligonucleotide and the polysaccharide according to the present invention is preferably carried out in the manner as detailed in PCT/JP02/02228 (Patent Reference 15). Thus, the polysaccharide typified by β-1,3-glucan, which originally assumes a triple helix structure as it occurs naturally or it is in water, is dissolved in a polar solvent (e.g. dimethyl sulfoxide) to unbind the structure to a single-stranded form, to which a single-stranded nucleic acid is added, followed by the replacement of the solvent by water (renaturation), thereby producing a complex of single-stranded nucleic acid and double-stranded polysaccharide, i.e., the complex suitable for use in the present invention (cf. Working Example 1 set out later). This complex is of noncovalent nature, in which the single-stranded nucleotide and the double-stranded polysaccharide are conjugated to each other to form a triple helix structure through hydrogen bonds and hydrophobic interactions. As the complex is prepared generally in the form of an aqueous solution, it can be highly purified by a relatively simple method such as ultrafiltration for therapeutic and other uses.

EXAMPLES

The characteristic features of the present invention will be more fully described with reference to the following working examples in terms of the preparation of concrete examples of the immunostimulating agents, the characterization of the immunostimulating agents prepared, and the evaluation of the agents administered in the in vitro tests. The examples are only for exemplifying purposes and not for restricting the invention.

Example 1

Preparation of Immunostimulating Agent Comprising a Complex of β-1,3-Glucan (Schizophyllan) and an Oligonucleotide Containing an Unmethylated CpG Motif Triple helix schizophyllan was prepared in accordance with the conventional method as described in the literature reference: Schizophyllum commune. Fies (ATCC 44200) available from ATCC (American Type Culture Collection), 10801 University Boulevard, Manassas, VA, 20110-2209, was subjected to a stationary culture in a minimal medium for seven days. After removal of the cellular materials and insoluble residues, the supernatant was subjected to a supersonic treatment to yield schizophyllan with a triple helix structure having a molecular weight of 450000.

The thus obtained schizophyllan was dissolved in dimethyl sulfoxide (hereinafter designated as DMSO) to form single-stranded schizophyllan and the concentration was adjusted to be 30 mg/ml. To 1 μl of the solution was added 3 μl of pure water, 1 μl of 10 mM Tris-buffer (pH 7.8) and 5 μl of 3 mg/ml CpG DNA solution. The solutions thus obtained were all clear and homogeneous (Gregory G. Martin, et al., Am. Chem. Soc. Polymer Prep. 38(1), 253-254 (1997); K. Tabata, et. al., Carbohydr., 89, 121-135 (1981)).

The CpG motif-containing oligonucleotide employed is a solid phase-synthesized product and has phosphorothioate bonds containing one dinucleotide sequence of cytosine-guanine (CpG). The total sequence is TCC ATG ACG TTC CTG ATG CT, with 3' terminal thereof being linked with forty dA's (SEQ ID No.1) (Y. Aramaki, et. al., Biol. Pharm. Bull., 25(3), 351-355 (2002).

Example 2

Synthesis of Cationic Derivative (Amino Group-Modified Schizophyllan) and Characterization A cationic derivative (schizophyllan modified with a cationic functional group) was synthesized in accordance with the reaction scheme shown in FIG. 1. It is possible to regulate the rate of introduction of amino group by regulating the equivalent number of sodium periodate for the periodate oxidation. Therefore, the same method of synthesis is applicable regardless of the rate of introduction. The present example relates to the synthesis of cationic functional group-modified schizophyllan in which the schizophyllan is introduced with amino groups at a rate of introduction of 4.6, 17, 20 and 36%. The amino group introduced was 2-aminoethanol or spermine. It is possible to regulate the rate of introduction of the amino group by regulating the equivalent number of the sodium periodate with respect to the branching glucose moiety. The experimental results are shown in Example 3.

In the manner as described in Example 1 was obtained schizophyllan having a molecular weight of 450000. 100 mg of the thus obtained schizophyllan was dissolved in 100 ml water. To the resultant solution was added slowly an aqueous solution of sodium periodate (in an equivalent of 10%, 40%, 50% or 500% (an excess amount) based on the branching glucose of the schizophyllan) and stirring was performed for two days at 4° C. The reaction solution was subjected to dialysis through a membrane (with an exclusion limit of 12000), followed by lyophilization. The white solid product was dissolved in 20 ml dimethyl sulfoxide. To the resultant solution was added 2 ml of 2-aminoethanol or spermine (a large excess: more than 10000 equivalents) and then stirring was performed for two days at room temperature. Then, there was added 100 mg sodium borohydride, followed by stirring for one day at room temperature. After the excess sodium borohydride was deactivated with acetic acid, the reaction solution was subjected to dialysis (acidic aqueous solution, basic aqueous solution and distilled water) through a membrane (exclusion limit: 12000), followed by lyophilization to yield the cationic derivative.

The rate of introduction of the amino group was determined on microanalysis of nitrogen by elemental analysis (low detection limit: 0.05%). The microanalysis of nitrogen was performed three times for each sample, with the results as shown Table 1. The molecular weight was examined through gel permeation chromatography (GPC) and also by measuring the viscosity, showing that it is identical to the molecular weight of the starting material.

TABLE 1

|  | Periodate Equivalent (%) | | | |
| --- | --- | --- | --- | --- |
|  | 10 | 40 | 80 | 500 |
| Amino Group Introduction Rate | 4.6-4.7 | 16.3-17.8 | 19.3-20.8 | 35.2-37.4 |

Example 3

Synthesis of Amino Acid Derivative (Arginine-Modified Schizophyllan) and Characterization In accordance with the reaction scheme, as shown in FIG. 1, an amino acid-derivative (schizophyllan modified with an amino acid-based functional group) was synthesized. The rate of introduction of the amino acid was regulated in the same manner as in Example 2. The present example relates to the synthesis of arginine-modified schizophyllan with rates of introduction of arginine of 4.6, 17, 20 and 36%.

In the manner as described in Example 1, there was obtained schizophyllan having a molecular weight of 450000. The thus obtained schizophyllan, 100 mg, was dissolved in 100 ml water. To the resultant solution was added slowly an aqueous solution of sodium periodate (in an equivalent of 10, 40 and 70% on the branching glucose of the schizophyllan) and stirring was performed for two days at 4° C. The reaction solution was subjected to dialysis through a membrane (exclusion limit: 12000), followed by lyophilization. The white solid product was dissolved in 20 ml DMSO. To the resultant solution was added 2 ml of arginine methyl ester (more than 10000 equivalents) followed by stirring for two days at room temperature. After the excess sodium borohydride was deactivated with acetic acid, the reaction solution was subjected to dialysis (acidic aqueous solution, basic aqueous solution, and distilled water) through a membrane (exclusion limit: 12000), followed by lyophilization to yield the arginine-modified schizophyllan.

The rate of introduction of arginine was determined on microanalysis of nitrogen by elemental analysis (lower detection limit: 0.05%). The microanalysis of nitrogen was performed three times for each sample. The results are shown in Table 2 (M. Numata, et al., Bioorg. Chem., 31, 163-171 (2003)).

TABLE 2

| Periodate Equivalent | Arginine Introduction Rate |
|---|---|
| 10% | 3.6% |
| 40% | 9.3% |
| 70% | 13.5% |

Example 4

Synthesis of Cholesterol Derivative (Cholesterol-Modified Schizophyllan) and Characterization In accordance with the scheme as shown in FIG. 1, a cholesterol derivative (schizophyllan modified with a steroid-based functional group) was synthesized. The rate of introduction of cholesterol was regulated in the same manner as in Example 2. The present example relates to the synthesis of cholesterol-modified schizophyllan in which the schizophyllan is introduced with cholesterol at the rate of introduction of 4.5%. Thus, 100 mg of schizophyllan, as prepared in the manner described in Example 1, was dissolved in 100 ml water. To the resultant solution was added sodium periodate 1.65 mg (5 mol % based on the branching glucose) and stirring was performed for two days at 4° C. in the dark. The reaction solution was subjected to dialysis through a membrane (exclusion limit: 12000), followed by lyophilization.

The white solid product was suspended in DMSO, followed by addition of a steroid-derivative terminated with an amino group (3β-cholest-5-en-3-yl-N-(2-aminethyl) carbamate as synthesized in the manner described in the literature reference by Ishi et al.) and stirring was performed for two days at room temperature. To the reaction solution was added 100 mg of sodium borohydride, two times at an interval of four hours, followed by stirring one day at room temperature. After the excess sodium borohydride was deactivated with acetic acid, the reaction solution was subjected to dialysis through a membrane (exclusion limit: 12000), followed by lyophilization (Tsutomu Ishii, Ritsuko Iguchi, Erwin Snip, Masato Ikeda and Seiji Shinkai, Langmuir, 17, 5825-5833 (2001)).

The rate of introduction of cholesterol was determined on microanalysis of nitrogen by elemental analysis (lower detection limit: 0.05%). The microanalysis of nitrogen was performed three times for each sample. The results are given in Table 3.

TABLE 3

| Periodate Oxidation Rate | Nitrogen Content | Cholesterol Introduction Rate |
|---|---|---|
| 5.0% | 0.358-0.383% | 4.5% |

Example 5

Synthesis of Peptides Containing Binding-Functional Group

In modifying schizophyllan with a peptide chain (peptide-based functional group), it is necessary for the peptide chain to have a functional group capable of binding to schizophyllan. While there are no special restrictions on the binding functional group and the spacer therefor, the present example relates to the synthesis of a peptide chain containing cysteine which includes a thiol moiety: The thiol covalently binds to a maleimide group by Michael addition.

Peptide sequences synthesized are an arginine oligomer which is known to have a high affinity to cell membrane (an octamer, referred to as R8: SEQ ID No.2), and a sequence of arginine-glycine-aspartic acid which is known as being recognized by cell adhesion factors (referred to as RGD: SEQ ID No.3), the two sequences being N-terminated with cysteine (cf. FIG. 2).

The peptide chains were synthesized by Fmoc method and the products were purified by HPLC (high performance liquid chromatography) (HITACHI L-700, ODS column available from YMC Co., eluting solvent: acetonitrile/distilled water=5/95 (both containing 0.1 vol % trifluoroacetate), forty minutes with a gradient of 20/80). Identification of the products was carried out by MALDI-TOF MS (matrix-assisted laser desorption ionization-time of flight mass spectrometer) (matrix:CHCA) with the results as shown in Table 4. See "Solid-phase Synthesis Handbook, published by Merck Co." for Fmoc method.

TABLE 4

| Peptide | Calculated | Found |
|---|---|---|
| R8 | 1371.65 | 1371.20 |
| RGD | 450.48 | 450.40 |

Example 6

Synthesis of Peptide-Modified Schizophyllan

Figure 3:
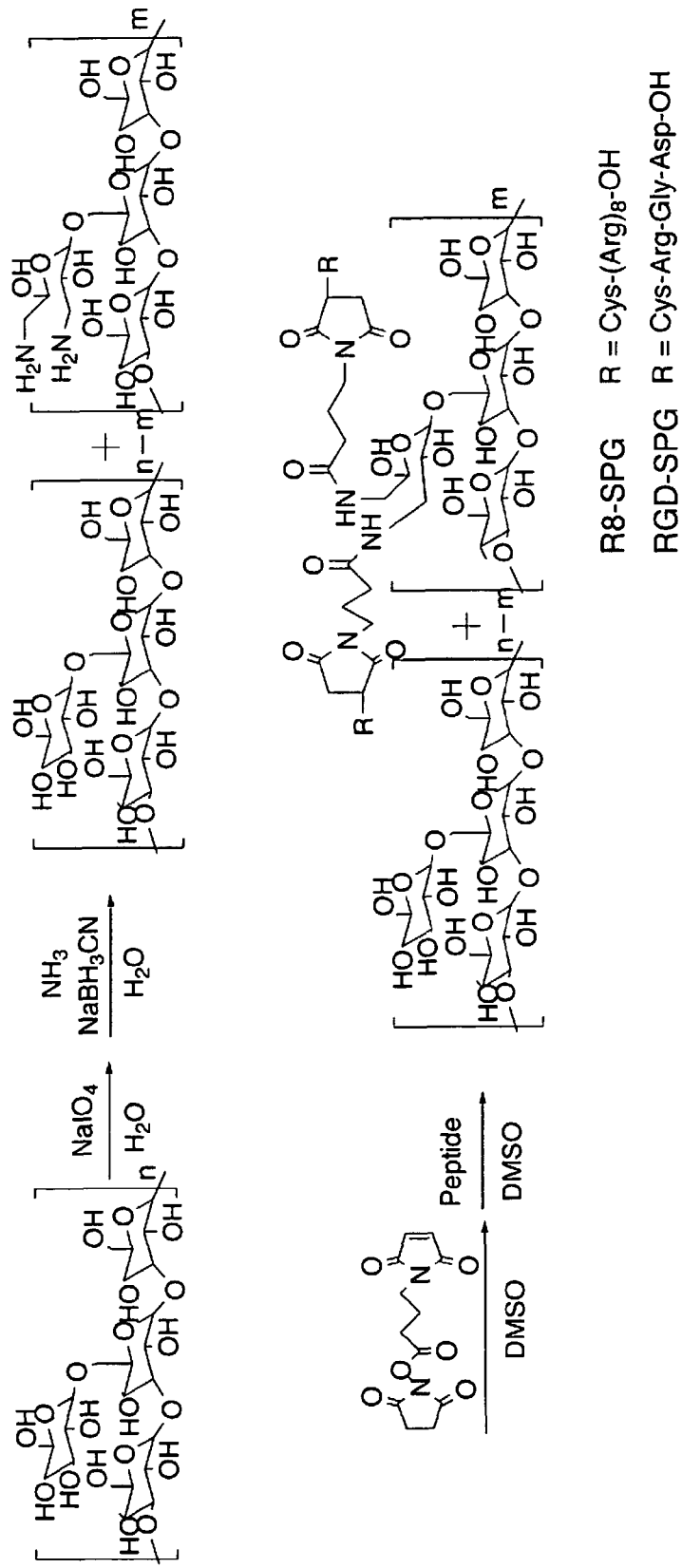
FIG. 3 shows an example of the reaction scheme for synthesizing peptide-modified schizophyllan (R8-SPG and RGD-SPG) for use in the present invention.

In accordance with the scheme shown by FIG. 3, the respective peptide-chains synthesized in Example 5 were introduced into schizophyllan. The reaction comprised the four steps of periodate oxidation, reductive amination, spacer introduction, and peptide introduction. The rate of introduction of peptide could be regulated by the periodate oxidation. The second and third steps were evaluated for the progress of reaction by elemental analysis. The results are shown in Example 7.

Schizophyllan 300 mg prepared in Example 1 was dissolved in 300 ml of water. To the resultant solution was added an aqueous solution of sodium periodate (9.87 mg: in an equivalent of 0.1 (10%) based on the branching glucose of the schizophyllan) and stirring was performed for two days at 4° C. under a lightproof condition. The reaction solution was subjected to dialysis through a membrane (exclusion limit: 12000), followed by lyophilization to yield a white solid 1.

The white solid product 1 (100 mg) was dissolved in 10 ml DMSO, a polar organic solvent, and 10 ml of 28% ammonia aqueous solution. To the resultant solution was added 200 mg (a large excess) of sodium cyanoborohydride, followed by stirring for four days at room temperature. The reaction solution was subjected to dialysis through a membrane (exclusion limit: 12000), followed by lyophilization to yield a white solid product 2.

The white solid product 2 was dissolved in 10 ml of DMSO. To the resultant solution was added 100 mg (a large excess) of 3-maleimide propionate-N-hydroxysuccinimide ester, followed by stirring for 24 hours at room temperature under a stream of nitrogen. The reaction solution was subjected to dialysis through a membrane (exclusion limit: 12000), followed by lyophilization to yield a white solid product 3.

The white solid product 3 was dissolved in 5 ml of DMSO. Each of the peptide chains containing cysteine as prepared in Example 5 was dissolved in distilled water. The thus obtained solution was mixed with the DMSO solution. The resultant solution was stirred for two days at room temperature. The reaction solution was subjected to dialysis through a membrane (exclusion limit: 12000), followed by lyophilization to yield each peptide-modified schizophyllan.

Example 7

Characterization of Peptide-Modified Schizophyllan

Characterization was performed for each peptide-modified schizophyllan prepared in Example 6, with respect to the rate of introduction at each step of the reaction by elemental analysis of nitrogen atom, as well as the molecular weight. Table 5 shows the rate of introduction of the functional groups (the rate of modification with the peptides) at the respective steps of the reaction, as measured by the elemental analysis of nitrogen. The molecular weights were evaluated by means of gel permeation chromatography, which showed that there was no substantial change in the molecular weight due to the peptide modification (T. Matsumoto, et al., Biochim. Biophys. Acta, 1670, 91-104 (2004)).

TABLE 5

| Schizophyllan | R8-modified Schizophyllan | | RGD-modified | |
|---|---|---|---|---|
| | Oxidation Rate of the Branch | | | |
| | 5% | 10% | 5% | 10% |
| White Solid Product 2 | 3.7 ± 0.1% | 9.4 ± 0.1% | 3.7 ± 0.1% | 9.4 ± 0.1% |
| White Solid Product 3 | 3.7 ± 0.3% | 2.3 ± 0.3% | 3.7 ± 0.3% | 2.3 ± 0.3% |
| Peptide-modified Schizophyllan | 0.3 ± 0.1% | 0.5 ± 0.1% | 1.0 ± 0.1% | 1.3 ± 0.3% |

Example 8

Preparation of Immunostimulating Agent Comprising CpG DNA Complexed with Cationized Schizophyllan, Amino Acid-Modified Schizophyllan, Cholesterol-Modified Schizophyllan or Peptide-Modified Schizophyllan In aliquots of DMSO were dissolved each of 17, 20 and 36% amino group-modified schizophyllan (hereinafter designated as N-SPG), 4.6% spermine-modified schizophyllan (hereinafter designated as SP-SPG), 3.6, 9.3 and 13.5% arginine-modified schizophyllan (hereinafter designated as Arg-SPG), 4.5% cholesterol-modified schizophyllan (hereinafter designated as Chol-SPG), 0.3 and 0.5% R8-modified schizophyllan (hereinafter designated as R8-SPG) and 1.0 and 1.3% RGD-modified schizophyllan (hereinafter designated as RGD-SPG) to form respective single-stranded modified schizophyllans and the concentration was adjusted to 30 mg/ml. Per 1 µl of each solution was added 3 µl of pure water, 1 µl of 10 mM Tris-buffer (pH 7.8) and 5 µl of the CpG DNA solution (3 mg/ml). The solutions thus obtained were all clear and homogeneous.

Hereinafter the schizophyllan derivatives as synthesized in Example 2, 3, 4 and 6 are collectively called as chemically modified schizophyllan. Each chemically modified schizophyllan is expressed by such a notation as "R8(0.3)-SPG" in which the numerical value within parentheses indicates the percentage of introduction of each functional group.

Example 9

Electrophoretical Confirmation of Formation of Complex Comprising CpG DNA and Schizophyllan As CpG DNA is negatively charged owing to the phosphoric acid groups, it migrates electrophoretically to the anode. Such migration occurs by passing through the network structure of the matrix gel, and therefore the formation of a complex of CpG DNA and schizophyllan reduces the mobility owing to increased molecular weight. Thus, with respect to the complexes of CpG DNA with schizophyllan or chemically modified schizophyllan prepared in the manners as described in Examples 1 and 8, the mobilities were evaluated by electrophoresis, in which the complexes were rendered to migrate on 2% agarose gel in MOPS buffer (20mM MOPS (pH 7.0), 5mM sodium acetate, 1mM EDTA, 3% dimethyl sulfoxide) for one hour at a voltage of 2v/cm. The gel was stained with GELSTAR™ Nucleic Acids Stain (BMA) and visualized on a transilluminator.

Figure 4:
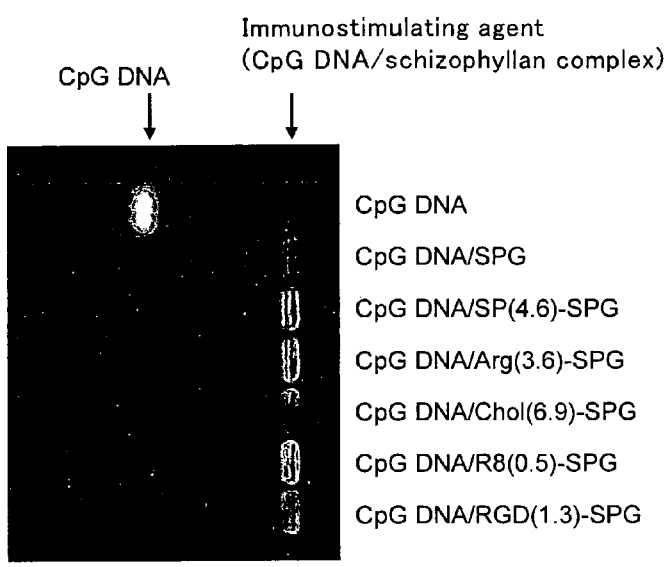
FIG. 4 is an agarose gel electropherogram showing that CpG DNA forms a complex with schizophyllan, amino group-modified schizophyllan, arginine-modified schizophyllan, R8-modified schizophyllan, or RGD-modified schizophyllan to compose an immunostimulating agent according to the present invention.

FIG. 4 shows an example of the results of the electrophoresis, from which it is seen that, when schizophyllan or chemically modified-schizophyllan was present, the mobilities decreased, thereby confirming the formation of the complexes.

Example 10

Enhanced Production of IL-12 Cytokine from Mouse-Derived Intraperitoneal Macrophage, Stimulated with a Complex of CpG DNA and Schizophyllan or Chemically Modified Schizophyllan The Isolation of the mouse-derived intraperitoneal macrophage was carried out in the ordinary manner as described in the literature reference. Thus, a female Balb/c mouse 8 weeks of age was sacrificed by bleeding from the carotid artery. Following sterilization with 70% ethanol, the abdominal skin was cleaved to expose the peritoneum. Cold PBS (phosphate buffered saline) 5 ml was injected into the peritoneum, followed by sufficient massage to harvest the fluid. Centrifugation was performed at 1,000 rpm for ten minutes at 4° C. using a polypropylene tube. After removal of the supernatant, the resultant was suspended in RPMI1640™ medium containing 10% fetal bovine serum ("New Biochemical Experiments 12: Molecular Immunology I, Immunocytes-Cytokines" edited by Biochemical Society of Japan, published by Tokyo Kagakudojin (1989): Non-patent Reference 22).

The thus obtained macrophage cells $2 \times 10^5$, having been suspended in 100μl of the PPMI1640™ medium containing 10% fetal bovine serum, were seeded into a 96-well plate and cultured under 5% $CO_2$ at 37° C. for two hours, so as to render the cells adhered to the plate. To the resultant were added CpG DNA and the complex of CpG DNA and schizophyllan or chemically modified schizophyllan as prepared in Examples 1 and 8, which had been subjected to ultrafiltration (exclusion limit: 3000) to remove the DMSO and readjusted with respect to the concentration. Culturing was conducted at 37° C. under 5% $CO_2$ for 24 hours, followed by the recovery of the culture supernatant.

Figure 5:
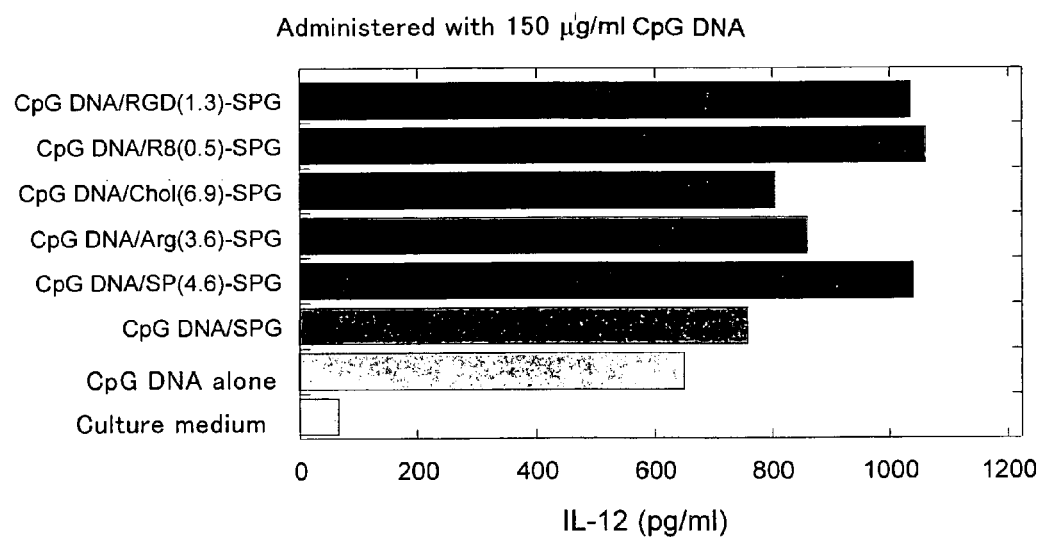
FIG. 5 demonstrates the enhanced production of IL-12 cytokine from mouse-derived intraperitoneal macrophage when stimulated with a complex of CpG DNA and schizophyllan or chemically modified schizophyllan, an immunostimulating agent according to the present invention.

The whole quantity of mouse-derived IL-12 contained in each culture supernatant was measured by utilizing Mouse Interleukin-12 Total ELISA (available from ENDOGEN), in which the measurement was carried out in accordance with the protocol attached. The results are shown in FIG. 5. As shown in FIG. 5, the total quantity of IL-12 contained in the culture supernatant was higher in the case where there was administered a complex of CpG DNA and schizophyllan or chemically modified schizophyllan, an immunostimulating agent of the present invention, as compared with the case of the administration of CpG DNA alone. It was thus evidenced from the results that the administration of the immunostimulating agent of the present invention enhances the production of cytokine (IL-12) from the macrophage.

Comparative Example 1

Figure 6:
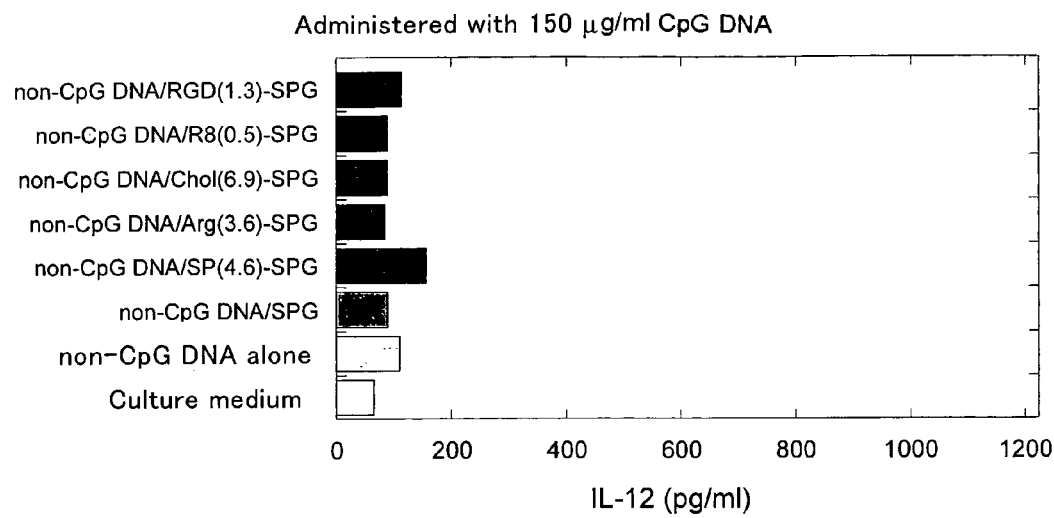
FIG. 6 shows the production of IL-12 cytokine from mouse-derived intraperitoneal macrophage when stimulated with a complex of non-CpG DNA (an oligonucleotide not containing any CpG motif) and schizophyllan or chemically modified schizophyllan.

Production of IL-12 Cytokine from Mouse-Derived Intraperitoneal Macrophage with a Complex of Non-CpG DNA (Oligonucleotide not Containing CpG Motif) and Schizophyllan or Chemically Modified Schizophyllan The production of IL-12 cytokine from mouse-derived intraperitoneal macrophage was evaluated in the same manner as in Example 10, by using a sequence of ATG AGC TTC CTG ATG CT, which has phosphorothioate bonds and does not contain any sequence of cytosine-guanine dinucleotide (CpG) (ie., is not immunostimulating), with the 3' terminus thereof being linked with forty dA's (hereinafter designated as non-CpG DNA: SEQ ID No. 18), in place of CpG DNA as used in Example 10. The results are shown in FIG. 6 (Y. Aramaki, et. al., Biol. Pharm. Bull., 25(3), 351-355 (2002): Non-patent Reference 23).

As shown in FIG. 6, there are observed no enhancing effects on the whole quantity of mouse IL-12 contained in the culture supernatant, even when administered with a complex of non-CpG DNA and schizophyllan or chemically modified schizophyllan, as well as with non-CpG DNA alone. The quantities are substantially the same level as that in the case of use of the culture medium alone without administration of such agents. It is thus evidenced from the results that the complexes composed of an oligonucleotide which is not immunostimulating (non-CpG DNA in the subject Example) will not be effective in immunostimulation (will not produce IL-12, a cytokine).

Example 11

Figure 7:
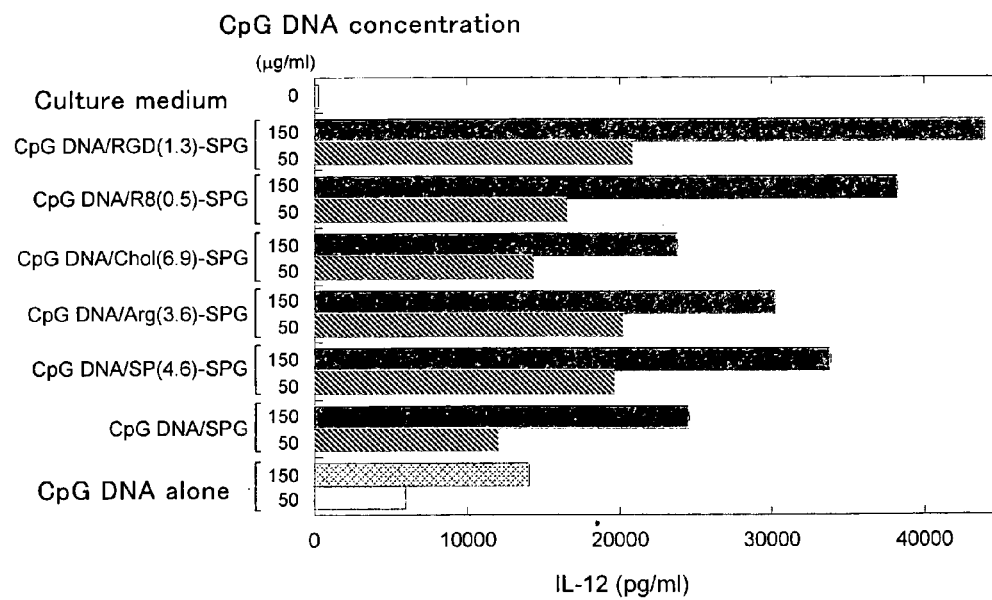
FIG. 7 demonstrates the enhanced production of IL-12 cytokine from a mouse-derived macrophage-like cell line J774.A1 when stimulated with a complex of CgG DNA and schizophyllan or chemically modified schizophyllan, an immunostimulating agent according to the present invention.

Enhanced Production of IL-12 Cytokine from Mouse-Derived Macrophage-Like Cell Line J774.A1, Stimulated with a Complex of CpG DNA and Schizophyllan or Chemically Modified Schizophyllan In the same manner as described in Example 10, the production of IL-12 cytokine was evaluated by using mouse-derived macrophage-like cell line J774.A1 (available from ATCC), which has been reported to enhance the production of IL-12 when treated with an immunostimulating substance, in place of mouse-derived intraperitoneal macrophage as used in Example 10. The results are shown in FIG. 7 (E. R. Kandimalla, et al., Bioconjugate Chem., 13(5), 966-974 (2002)).

As shown in FIG. 7, the whole quantity of IL-12 contained in the culture supernatant is higher in the case where there is administered a complex of CpG DNA and schizophyllan or chemically modified schizophyllan, an immunostimulating agent of the present invention, as compared with the case of the administration of CpG DNA alone. It is thus evidenced from the results that the administration of the immunostimulating agent of the present invention enhances the production of cytokine (IL-12) from the macrophage, as well as from the mouse-derived intraperitoneal macrophage as shown in Example 10.

Example 12

Enhanced Production of IL-6 and IL-12 Cytokines from Mouse-Derived Spleen Cells, Stimulated with a Complex of CpG DNA and Schizophyllan or Chemically Modified Schizophyllan In the same manner as described in Example 10, the production of IL-6 and IL-12 cytokines was evaluated by using mouse-derived spleen cells (spleen lymphocytes), which have been reported to enhance the production of IL-6 and IL-12 when treated with an immunostimulating substance, in place of mouse-derived intraperitoneal macrophage as used Example 10.

The Isolation of the mouse-derived spleen cells was carried out in the ordinary manner as described in the literature reference. Thus, a female Balb/c mouse 8 weeks of age was sacrificed by cervical dislocation. Following sterilization with 70% ethanol, the abdominal skin was cleaved to expose the peritoneum. The spleen was excised from the peritoneum. The spleen was loosened with a net (200 mesh) and tweezers in PBS, and then the cell cluster was filtered through the net. The cell suspension was subjected to centrifugation at 1,000 rpm for ten minutes at 4° C., using a polypropylene tube. After removal of the supernatant, the resultant was suspended in RPMI1640 medium containing 10% fetal bovine serum ("New Biochemical Experiments 12: Molecular Immunology I, Immunocytes-Cytokines" edited by Biochemical Society of Japan, published by Tokyo Kagakudojin (1989)).

The thus obtained mouse-derived spleen cells $2.5 \times 10^5$, having been suspended in 100 μl of the RPMI1640 medium containing 10% fetal bovine serum, were seeded into a 96-well plate. To the resultant were added CpG DNA and the complex of CpG DNA and schizophyllan or chemically modified schizophyllan as prepared in Examples 1 and 8, which had been subjected to ultrafiltration (extrusion limit 3000) to remove the DMSO and readjusted with respect to the concentration. Culturing was conducted at 37° C. under 5% $CO_2$ for 24 hours, followed by the recovery of the culture supernatant.

Figure 8:
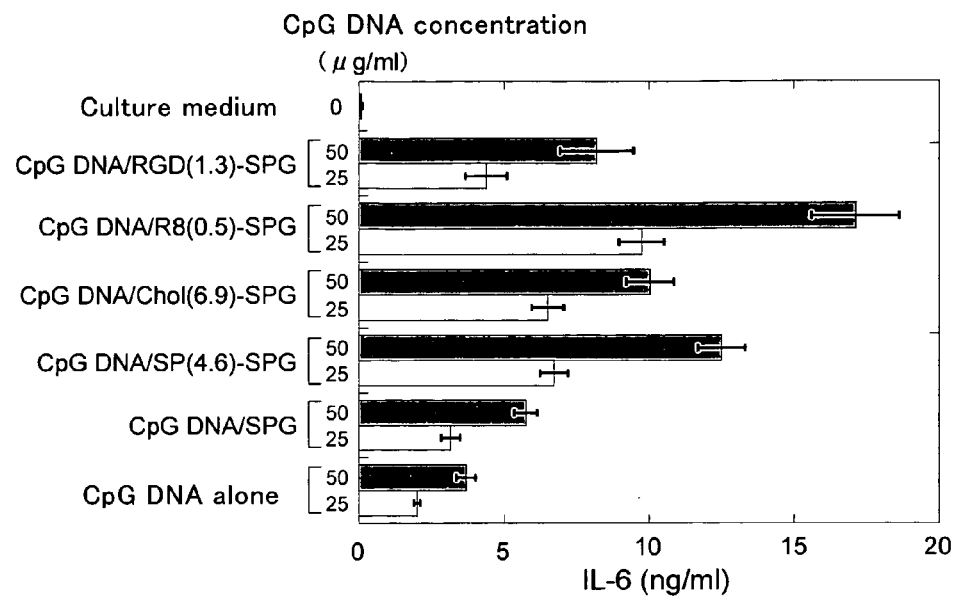
FIG. 8 demonstrates the enhanced production of cytokine IL-6 from mouse-derived spleen cells when stimulated with a complex of CpG DNA and schizophyllan or chemically modified schizophyllan, an immunostimulating agent according to the present invention.
Figure 9:
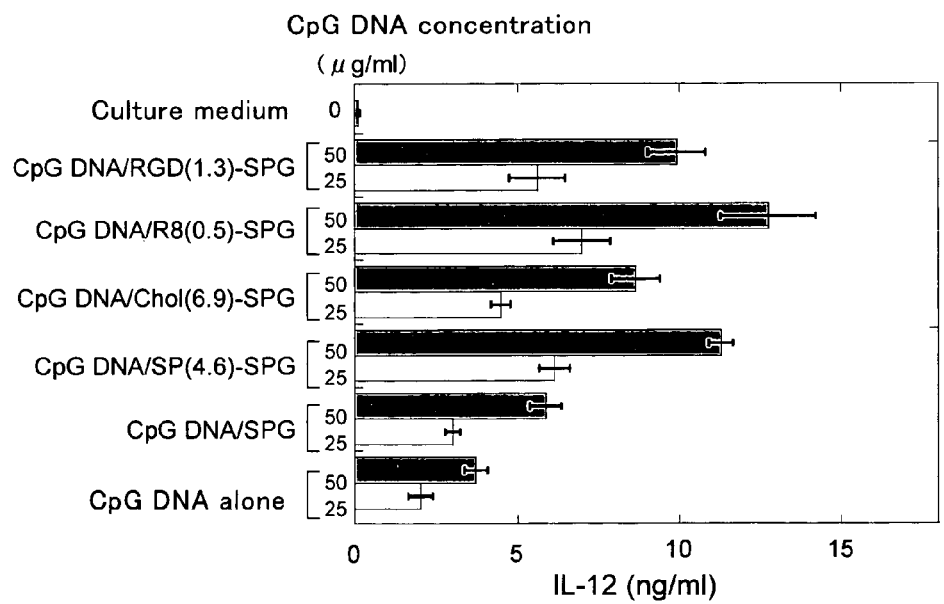
FIG. 9 demonstrates the enhanced production of cytokine IL-12 from mouse-derived spleen cells when stimulated with a complex of CpG DNA and schizophyllan or chemically modified schizophyllan, an immunostimulating agent according to the present invention.

The whole quantities of mouse-derived IL-6 and IL-12 contained in each culture supernatant were measured by utilizing Mouse Interleukin-6 Total ELISA and Mouse Interleukin-12 Total ELISA (available from ENDOGEN), in which the measurement was carried out in accordance with the protocol attached. The results are shown in FIG. 8 and FIG. 9. As shown in FIG. 8 and FIG. 9, the whole quantities of IL-6 and IL-12 contained in the culture supernatant were higher in the case where there was administered a complex of CpG DNA and schizophyllan or chemically modified schizophyllan, an immunostimulating agent of the present invention, as compared with the case of the administration of CpG DNA alone. It was thus evidenced from the results that the administration of the immunostimulating agent of the present invention enhances the production of cytokines (IL-6 and IL-12) from the spleen cells (lymphocytes) (E. R. Kandimalla, et al., Bioconjugate Chem., 13(5), 966-974 (2002)).

Comparative Example 2

Production of IL-6 and IL-12 Cytokines from Mouse-Derived Spleen Cells, with a Complex of Non-CpG DNA and Schizophyllan or Chemically Modified Schizophyllan The production of IL-6 and IL-12 cytokines from mouse-derived spleen cells was evaluated in the same manner as in Example 12, by using non-CpG DNA in place of CpG DNA as used in Example 12. The results are shown in FIG. 10 and FIG. 11.

Figure 10:
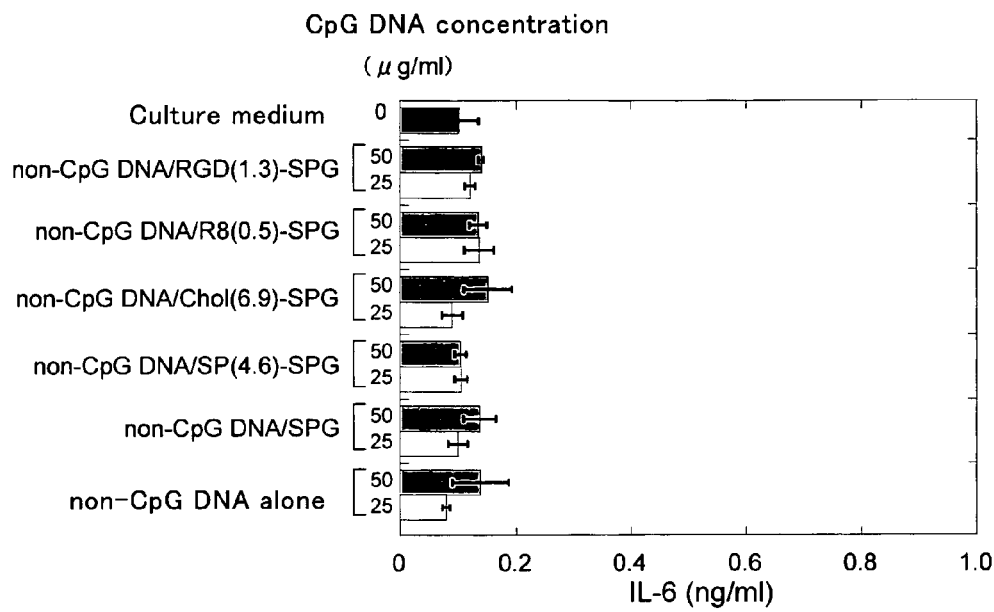
FIG. 10 shows the production of cytokine IL-6 from mouse-derived spleen cells when stimulated with a complex of non-CpG DNA and schizophyllan or chemically modified schizophyllan.
Figure 11:
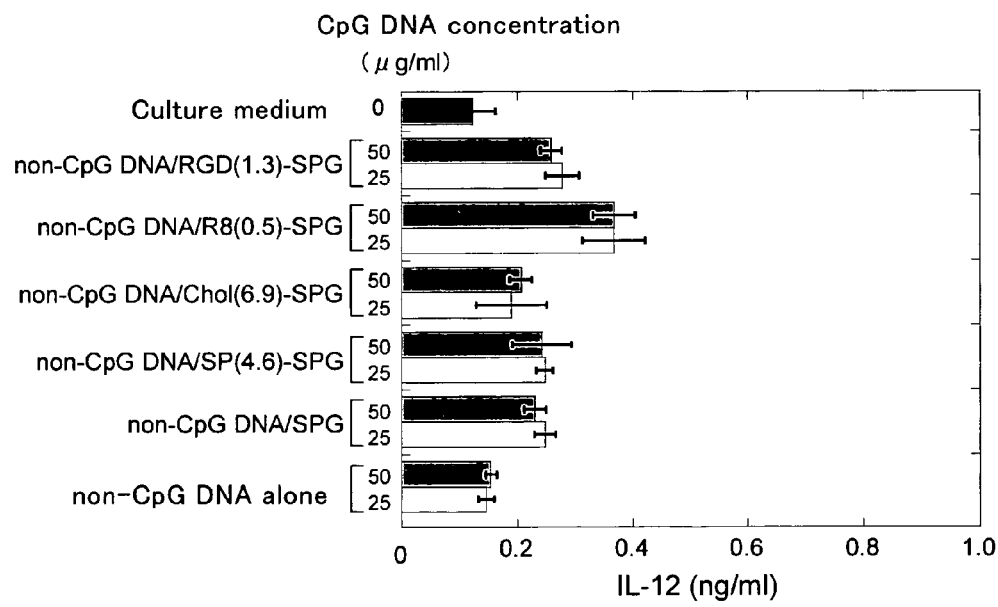
FIG. 11 shows the production of cytokine IL-12 from mouse-derived spleen cells when stimulated with a complex of non-CpG DNA and schizophyllan or the chemically modified schizophyllan.

As shown in FIG. 10 and FIG. 11 there were observed no enhancing effects on the whole quantity of mouse IL-6 and IL-12 contained in the culture supernatant, even when administered with a complex of non-CpG DNA and schizophyllan or chemically modified schizophyllan, as well as with non-CpG DNA alone. The quantities of IL-6 and IL-12 were substantially the same level as that in the case of use of the culture medium alone without administration of such agents. It was thus evidenced from the results that the complexes composed of an oligonucleotide which is not immunostimulating (non-CpG DNA in the subject Example) are not effective in immunostimulation.

Example 13

Preparation of Immunostimulating Agent Comprising a Complex of β-1,3-Glucan (Schizophyllan) or Chemically Modified Schizophyllan and Phosphodiester-Bonded CpG DNA (CpG DNA (PO))

Each of schizophyllan and chemically modified schizophyllan was dissolved in DMSO to form a single-stranded structure and the concentration was adjusted to be 30 mg/ml. To 1 μl of the thus obtained solution were added 3 μl of pure water, 1 μl of 10 mM Tris-buffer (pH 7.8) and 5 11 of CpG DNA (PO) solution (3 mg/ml), in place of CpG DNA solution as described in Example 1. The solutions thus obtained were all clear and homogeneous.

The CpG motif-containing oligonucleotide (a solid phase-synthesized product) contained one sequence of cytosine-guanine (CpG), in which the total sequence was phosphodiester-bonded TCC ATG ACG TTC CTG ATG CT, with the 3'-terminus thereof being linked with forty dA's (CpG DNA (PO): SEQ ID No.5).

Example 14

Enhanced Production of IL-6 and IL-12 Cytokines from Mouse-Derived Spleen Cells, Stimulated with a Complex of CpG DNA (PO) and Schizophyllan or Chemically Modified Schizophyllan In the same manner as described in Example 12, the production of IL-6 and IL-12 from mouse-derived spleen cells was evaluated with CpG DNA (PO) complex as prepared in Example 13 in place of CpG DNA complex as used in Example 12. The results are shown in FIG. 12 and FIG. 13.

Figure 12:
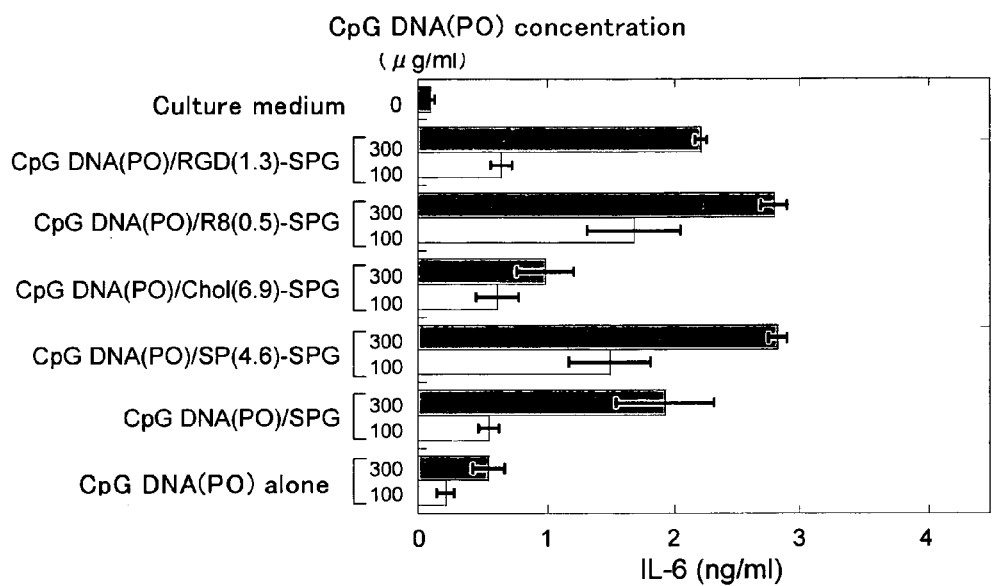
FIG. 12 demonstrates the enhanced production of cytokine IL-6 from mouse-derived spleen cells when stimulated with a complex of CpG DNA (PO) (CpG DNA having phosphodiester bonds) and schizophyllan or chemically modified schizophyllan, an immunostimulating agent according to the present invention.
Figure 13:
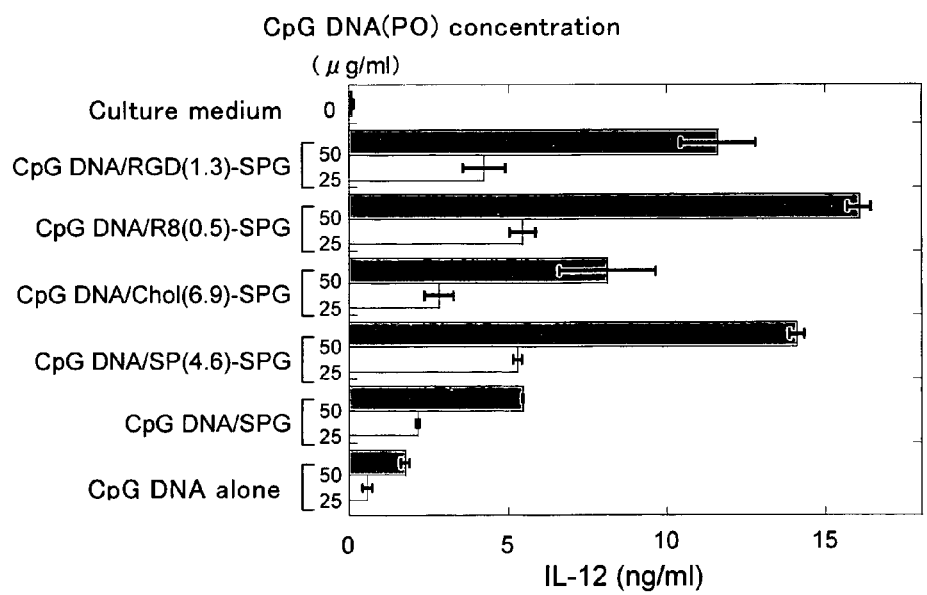
FIG. 13 demonstrates the enhanced production of cytokine IL-12 from mouse-derived spleen cells when stimulated with a complex of CpG DNA(PO) and schizophyllan or chemically codified schizophyllan, an immunostimulating agent according to the present invention.

As shown in FIG. 12 and FIG. 13, the whole quantities of IL-6 and IL-12 contained in the culture supernatant were higher in the case where there was administered a complex of CpG DNA (PO) and schizophyllan or chemically modified schizophyllan, an immunostimulating agent of the present invention, as compared with the case of the administration of CpG DNA (PO) alone. It was thus evidenced that the administration of the immunostimulating agent comprising CpG DNA (PO)/schizophyllan complex or CpG DNA (PO)/chemically modified complex enhances the production of cytokines (IL-6 and IL-12) from the mouse-derived spleen cells.

Comparative Example 3

Production of IL-6 and IL-12 Cytokines from Mouse-Derived Spleen Cells, with a Complex of Non-CpG DNA (PO) and Schizophyllan or Chemically Modified Schizophyllan In the same manner as described in Example 14, the production of IL-6 and IL-12 cytokines from the mouse-derived spleen cells was evaluated by using an oligonucleotide not containing any sequence of cytosine-guanine dinucleotide (CpG), in which the total sequence was phosphodiester-bonded TCC ATG AGC TTC CTG ATG CT with the 3'-terminus thereof being linked with forty dA's (hereinafter designated as non-CpG DNA (PO): SEQ ID No.6), in place of CpG DNA (PO) as used in Example 14. The results are shown in FIG. 14 and FIG. 15.

Figure 14:
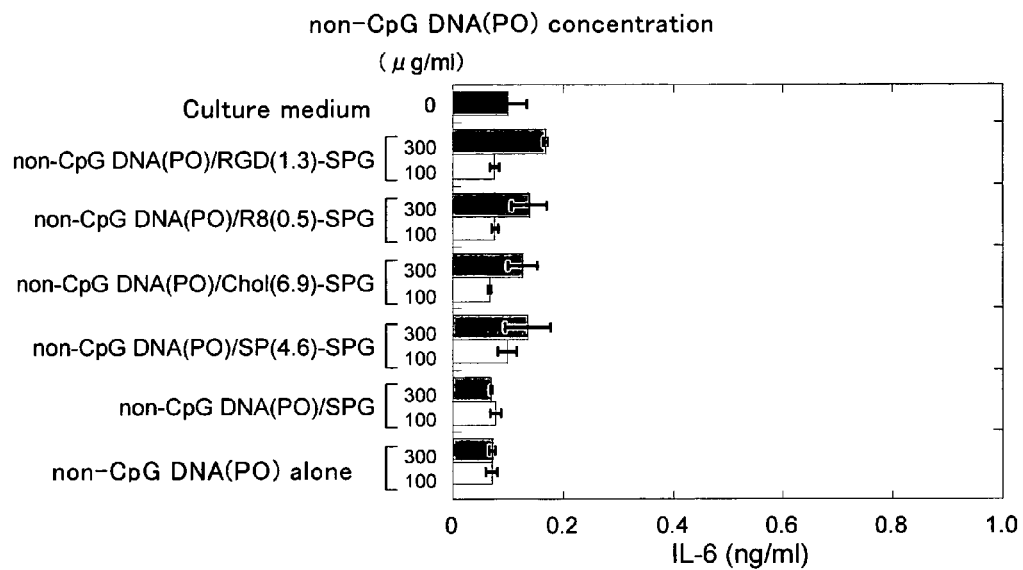
FIG. 14 shows the production of cytokine IL-6 from mouse-derived spleen cells when stimulated with a complex of non-CpG DNA(PO) (CpG DNA having phosphodiester bonds and not having any CpG motif) and schizophyllan or chemically modified schizophyllan.
Figure 15:
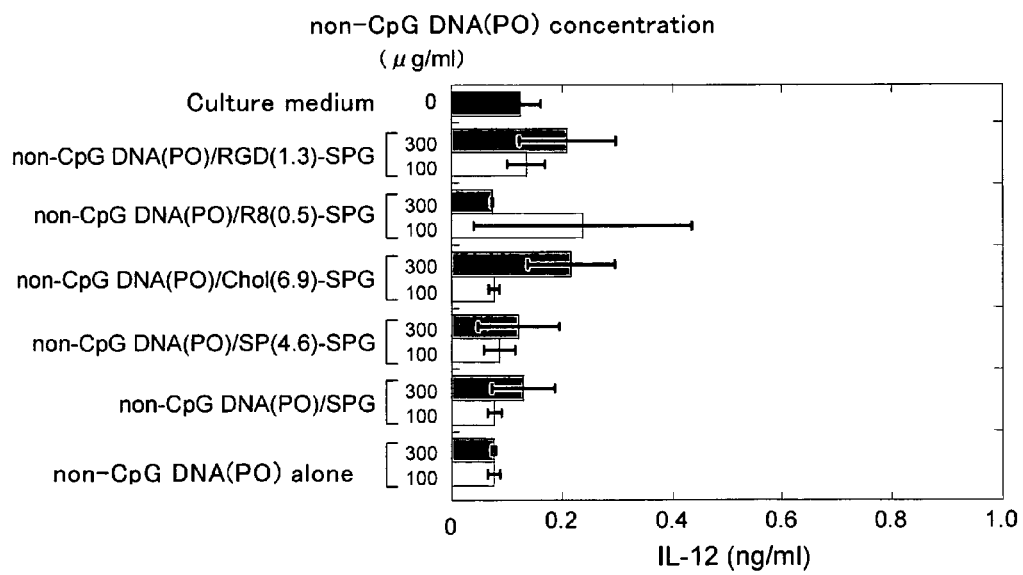
FIG. 15 shows the production of cytokine IL-12 from mouse-derived spleen cells when stimulated with a complex of non-CpG DNA(PO) and schizophyllan or chemically modified schizophyllan.
Figure 16:
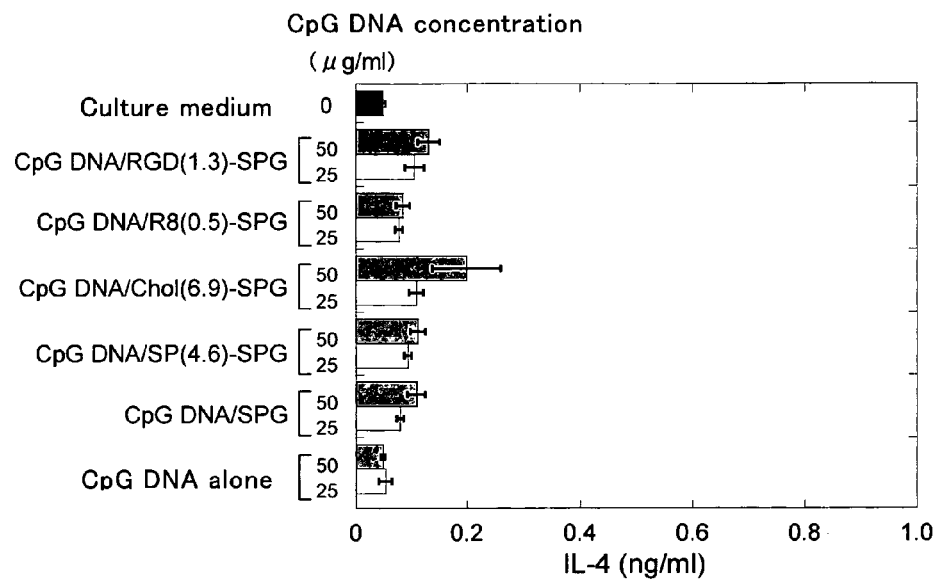
FIG. 16 demonstrates the enhanced production of cytokine IL-4 from mouse-derived spleen cells when stimulated with a complex of CpG DNA and schizophyllan or chemically modified schizophyllan, an immunostimulating agent according to the present invention.
Figure 17:
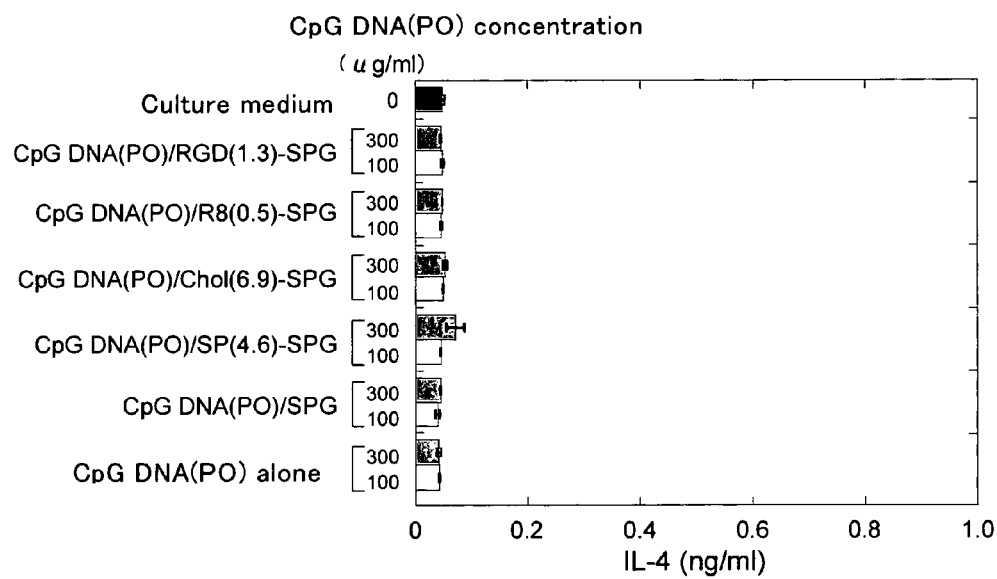
FIG. 17 shows the production of cytokine IL-4 from mouse-derived spleen cells when stimulated with a complex of CpG DNA(PO) and schizophyllan or chemically modified schizophyllan, an immunostimulating agent according to the present invention.
Figure 18:
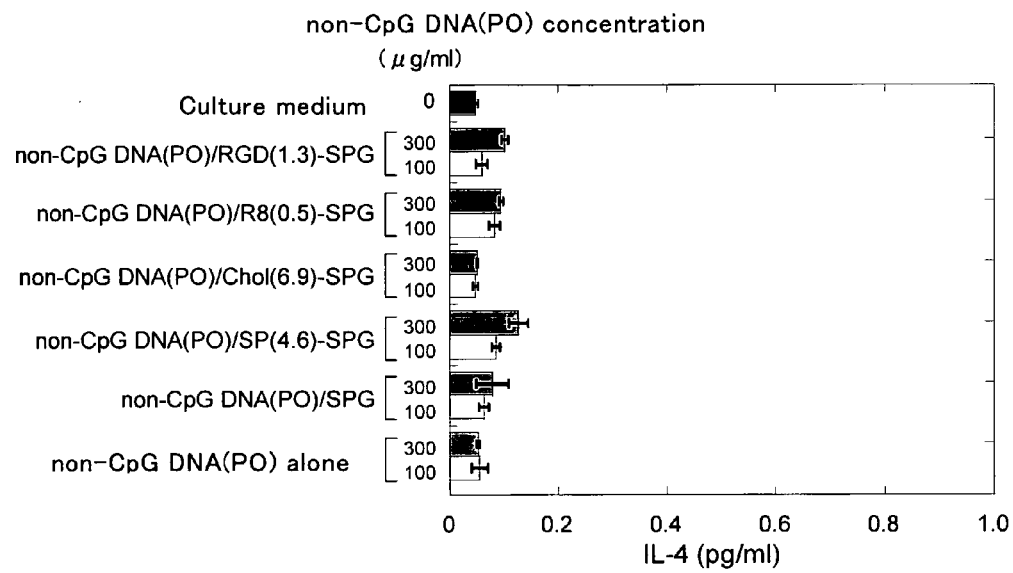
FIG. 18 shows the production of cytokine IL-4 from mouse-derived spleen cells when stimulated with a complex of non-CpG DNA and schizophyllan or chemically modified schizophyllan.
Figure 19:
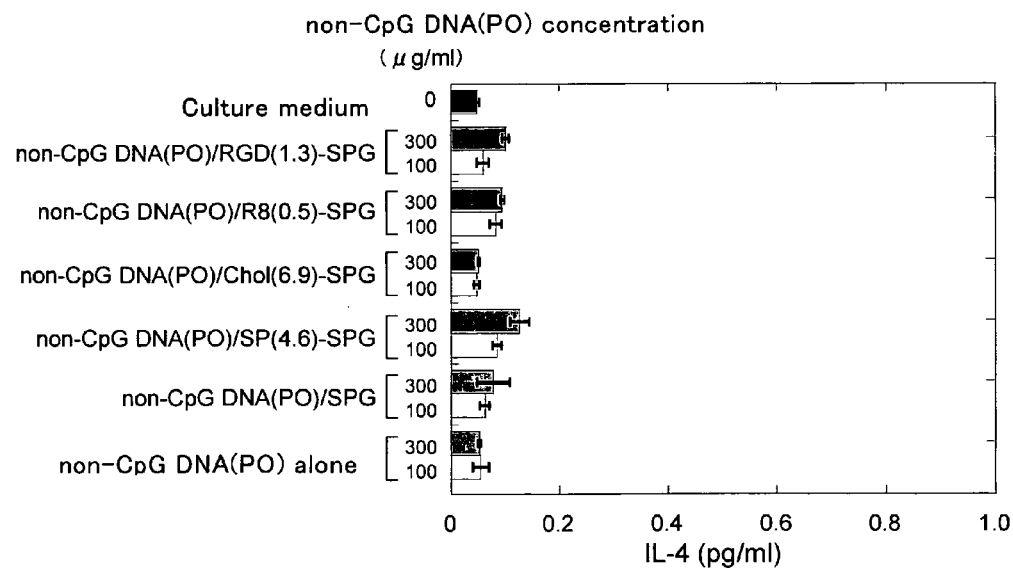
FIG. 19 shows the production of cytokine IL-4 from mouse-derived spleen cells when stimulated with a complex of non-CpG DNA(PO) and schizophyllan or chemically modified schizophyllan.

As shown in FIG. 14 and FIG. 15, there was observed no enhancing effect on the whole quantity of mouse IL-6 and IL-12 contained in the culture supernatant even when administered with a complex of non-CpG DNA (PO) and schizophyllan or chemically modified schizophyllan, as well as with non-CpG DNA (PO) alone. The quantities were substantially the same level as that in the case of use of the culture medium alone without administration of such agents. It was thus evidenced from the results that the complexes composed of an oligonucleotide which is not immunostimulating (non-CpG DNA (PO)) is not effective in immunostimulation (i.e. does not produce IL-6 and IL-12 cytokines).

Comparative Example 4

Production of IL-4 Cytokine from Mouse-Derived Spleen Cells, with CpG DNA, CpG DNA (PO), Non-CpG DNA or Non-CpG DNA (PO) Complexed with Schizophyllan or Chemically Modified Schizophyllan In the same manner as described in Example 12 and Example 14, the production of IL-4 from the mouse-derived spleen cells is evaluated with the agents. The results are shown in FIG. 16 through FIG. 19.

As shown in FIG. 16 through FIG. 19, there are observed no significantly enhancing effects on the whole quantity of mouse IL-4 contained in the culture supernatant, even when administered with CpG DNA, CpG DNA (PO), non-CpG DNA or non-CpG DNA (PO) complexed with schizophyllan or chemically modified schizophyllan, as well as with CpG DNA, CpG DNA(PO), non-CpG DNA or non-CpG DNA (PO) alone. The quantities are almost the same level as that in the case of use of the culture medium alone without administration of such agents. It has been reported that while CpG motif which is immunoactive will induce the production of cytokines due to cellular immunity (type-I immunity) such as IL-2, IL-12, TNF-α, IFN-γ and so on, it will suppress cytokines due to humoral immunity (type-II immunity) such as IL-4, IL-5, IL-10, IL-13 and so on. The above-mentioned results support that the administration of an immunostimulating agent of the present invention enhances immunity owing to such immunostimulating effect of the CpG motif.

INDUSTRIAL UTILITY

The present invention provides a new type of immunostimulating agent comprising, as carrier (transfection agent), a polysaccharide such as β-1,3-glucan, the safety of which has been established. The immunostimulating agent of the present invention is safe and exhibits an excellent efficacy in immunological enhancement, and therefore has prospective applications in such area as immunotherapy and gene therapy.

---

The invention claimed is:

1. An immunostimulating agent which comprises a complex of an immunostimulating oligonucleotide of 8 to 100 nucleotides which contains an unmethylated CpG motif and a polysaccharide having β-1,3-bonds.

2. The immunostimulating agent of claim 1, wherein the phosphoric acid backbone of the oligonucleotide is phosphorothioate-modified or phosphorodithioate-modified.

3. The immunostimulating agent of claim 1, wherein the polysaccharide having β-1,3-bonds is β-1,3-glucan or β-1,3-xylan.

4. The immunostimulating agent of claim 1, wherein the β-1,3-glucan is selected from among schizophyllan, curdlan, lentinan, pachyman, grifolan, laminaran and scleroglucan.

5. The immunostimulating agent of claim 1, wherein the polysaccharide is modified with nucleic acid-binding functional group and/or cell membrane-affinitive functional group.

6. The immunostimulating agent of claim 1, wherein the complex of the oligonucleotide and the polysaccharide is of a triple helix structure formed through hydrogen bonds and hydrophobic interactions.

7. The immunostimulating agent of claim 1, wherein said unmethylated CpG motif is selected the group consisting of AACGTT, AGCGTT, GACGTT, GGCGTT, AACGTC, AGCGTC, GACGTC, GGCGTC, AACGCC, AGCGCC, GACGCC, GGCGCC, AACGCT, AGCGCT, GACGCT, and GGCGCT.

8. The immunostimulating agent of claim 1, wherein said immunostimulating oligonucleotide is selected from the group consisting of:

accgataccggtgccggtgacggcaccacg; (SEQ ID NO 7)

accgatagcgctgccggtgacggcaccacg; (SEQ ID NO 8)

accgatgacgtcgccggtgacggcaccacg; (SEQ ID NO 9)

accgattcgcgagccggtgacggcaccacg; (SEQ ID NO 10)

ggggggggggggcgatcggggggggggggg; (SEQ ID NO 11)

ggggggggggggacgatcgtcgggggggggg; (SEQ ID NO 12)

ggggggggggggaacgttgggggggggggg; (SEQ ID NO 13)

GAGAACGCTCGACCTTCGAT; (SEQ ID NO 14)

TCCATGACGTTCCTGATGCT; and (SEQ ID NO 15)

TCTCCCAGCGTGCGCCAT; (SEQ ID NO 16)

wherein capital letters denote a thiolated DNA.

9. The immunostimulating agent of claim 1, wherein the polysaccharide to be complexed is provided with nucleic acid-binding functional groups formed by periodate oxidation of 1,6-glucopyranoside branches followed by reductive amination.

* * * * *